(12) United States Patent
Carol et al.

(10) Patent No.: US 6,261,300 B1
(45) Date of Patent: *Jul. 17, 2001

(54) APPARATUS AND METHOD FOR SURGICAL STEREOTACTIC PROCEDURES

(75) Inventors: Mark Carol, Sewickley, PA (US); James L. Day, Cincinnati, OH (US); Erik G. Miller; Robert J. Riker, both of Pittsburgh, PA (US)

(73) Assignee: Ohio Medical Instrument Company, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/553,508

(22) Filed: Apr. 20, 2000

Related U.S. Application Data

(62) Division of application No. 08/986,292, filed on Dec. 6, 1997, now Pat. No. 6,071,288, which is a continuation of application No. 08/315,927, filed on Sep. 30, 1994, now Pat. No. 5,695,501.

(51) Int. Cl.$^7$ .................................................. A61B 19/00
(52) U.S. Cl. ........................ 606/130; 600/417; 600/429
(58) Field of Search ................... 606/130, 1; 600/417, 600/429

(56) References Cited

U.S. PATENT DOCUMENTS

| | | |
|---|---|---|
| 1,129,333 | 2/1915 | Clarke . |
| 3,135,263 | 6/1964 | Connelley . |
| 3,223,087 | 12/1965 | Vladyka et al. . |
| 3,508,552 | 4/1970 | Hainault . |
| 4,341,220 | 7/1982 | Perry . |
| 4,386,602 | 6/1983 | Sheldon et al. . |
| 4,463,758 | 8/1984 | Patil et al. . |
| 4,475,550 | 10/1984 | Bremer et al. . |
| 4,608,977 | 9/1986 | Brown . |
| 4,617,925 | 10/1986 | Laitinen . |

(List continued on next page.)

FOREIGN PATENT DOCUMENTS

| | | |
|---|---|---|
| 427358 | 5/1991 | (EP) . |
| 609085 | 8/1994 | (EP) . |
| WO8809151 | 1/1988 | (WO) . |

OTHER PUBLICATIONS

Hwa–Shain Yeh et al., Implantation of Intracerebral Depth Electrodes for Monitoring Seizures Using the Pelorus Stereotatic System Guided by Magnetic Resonance Imaging, J. Neurosurg 78:138–141, 1993.

Robert T. Malison et al., Computer–Assisted Coregistration of Multislice SPECT and MR Brain Images by Fixed External Fiducials, Journal of Computer Assisted Tomography 17(6):952–960, Nov./Dec. 1993.

*Primary Examiner*—Pedro Philogene
(74) *Attorney, Agent, or Firm*—Wood, Herron & Evans, L.L.P.

(57) ABSTRACT

An apparatus and method are disclosed for displaying a path between a selected target and selected points on a patient's skull and for guiding surgical instruments along any selected path. The system is comprised of an image display system, an articulated arm and probe, and a stereotactic system. The sub-systems are coupled to one another so that the articulated probe may be used to select patient fiducial points that correspond to selected image fiducial points. Using these points, the image display system coregisters the external locations to the displayed images so that the probe condition may be displayed with the displayed images. The system further permits the identification of a selected target within a patient's brain and to project a path from the external position to the target prior to the performance of a craniotomy. After evaluation of the path, a surgeon may lock the stereotactic system in place to preserve a selected surgical path and to guide instruments along that path. A method of utilizing the system to perform such surgical procedures is also described.

32 Claims, 3 Drawing Sheets

(1 of 3 Drawing Sheet(s) Filed in Color)

U.S. PATENT DOCUMENTS

| | | |
|---|---|---|
| 4,618,978 | 10/1986 | Cosman . |
| 4,706,665 | 11/1987 | Gouda . |
| 4,733,661 | 3/1988 | Palestrant . |
| 4,805,615 | 2/1989 | Carol . |
| 4,955,891 | 9/1990 | Carol . |
| 4,991,579 | 2/1991 | Allen . |
| 4,998,938 | 3/1991 | Ghajar et al. . |
| 5,006,122 | 4/1991 | Wyatt et al. . |
| 5,027,818 | 7/1991 | Bova et al. . |
| 5,050,608 | 9/1991 | Watanabe et al. . |
| 5,078,140 | 1/1992 | Kwoh . |
| 5,080,662 | 1/1992 | Paul . |
| 5,116,345 * | 5/1992 | Jewell et al. ................. 606/130 |
| 5,163,430 | 11/1992 | Carol . |
| 5,186,174 | 2/1993 | Schlondorff et al. . |
| 5,207,223 | 5/1993 | Alder . |
| 5,207,688 | 5/1993 | Carol . |
| 5,222,499 | 6/1993 | Allen et al. . |
| 5,230,623 | 7/1993 | Guthrie et al. . |
| 5,257,998 | 11/1993 | Ota et al. . |
| 5,263,956 | 11/1993 | Nobles . |
| 5,269,305 | 12/1993 | Carol . |
| 5,279,309 | 1/1994 | Taylor et al. . |
| 5,300,080 | 4/1994 | Clayman et al. . |
| 5,361,763 | 11/1994 | Kao et al. . |
| 5,387,220 | 2/1995 | Pisharudi . |
| 5,452,720 | 9/1995 | Smith et al. . |
| 5,474,564 | 12/1995 | Clayman et al. . |
| 5,494,034 | 2/1996 | Schlondorff et al. . |
| 5,517,990 | 5/1996 | Kalfas et al. . |
| 5,618,288 * | 4/1997 | Calvo ................................ 606/130 |
| 5,622,170 | 4/1997 | Schulz . |
| 5,695,501 * | 12/1997 | Carol et al. ..................... 606/130 |
| 5,776,064 | 7/1998 | Kalfas et al. . |
| 5,851,183 | 12/1998 | Bucholz . |
| 5,873,822 | 2/1999 | Ferre et al. . |
| 5,891,034 | 4/1999 | Bucholz . |
| 5,891,157 * | 4/1999 | Day et al. ........................ 606/130 |
| 5,984,930 * | 11/1999 | Maciunas et al. ............... 606/130 |
| 6,071,288 * | 6/2000 | Carol et al. ..................... 606/130 |
| 6,110,182 * | 8/2000 | Mowlai-ashtiani .............. 606/130 |
| 6,117,143 * | 9/2000 | Hynes et al. .................... 606/130 |
| 6,120,465 | 9/2000 | Guthrie et al. . |

\* cited by examiner

APPARATUS AND METHOD FOR SURGICAL STEREOTACTIC PROCEDURES

This application is a Division of U.S. Patent Application Ser. No. 08/986,292, filed on Dec. 6, 1997 U.S. Pat. No. 6,071,288; which is a Continuation of U.S. Patent Application Ser. No. 08/315,927, filed on Sep. 30, 1994, now U.S. Pat. No. 5,695,501.

FIELD OF THE INVENTION

This invention relates to neurosurgical apparatus generally, and more particularly, to stereotactic systems for use in neurosurgery.

BACKGROUND OF THE INVENTION

During the 1970's radiological imaging systems were developed to assist surgeons in ascertaining the internal condition of a patient in greater detail. Specifically, computer assisted tomography (CAT) systems were developed to enhance images generated from data produced during a radiological scan of a patient. The patient is placed within a gantry, and a radiation source and radiation detectors are positioned opposite one another to be rotated about a portion of the patient's body. The data generated by the radiation detectors are utilized by a computer to generate radiographic images or "slices" of the body position to give a doctor greatly enhanced views through the area of interest.

Later radiographic imaging systems included magnetic resonance (MRI) and positron emission tomography (PET) imaging which generate images from energy sources that do not use x-rays or the like. These devices are useful because they provide different or additional information about organs or tissues than CAT scan images. In this application the term scanners refers to imaging devices regardless of the technique utilized to generate the images.

Neurosurgery may be performed to investigate, repair, or remove anomalies located within the brain of a patient. The environment of such surgeries is challenging in that the organ of interest, the brain, is surrounded by relatively thick bony structure, the skull. The only presurgery access to the brain available to a surgeon is through images generated by an imaging system.

Because of the inaccessibility, size, and roughly hemispherical shape of the brain, specifying the locus of a point inside the brain generally requires reference to some fixed external reference system. To provide a surgeon with sufficient information to locate an area of interest on an image, such as a tumor or lesion, a variety of systems have been developed to provide a reference point or points which may be used to match the patient's anatomical structure with the structures displayed in the images. These systems typically require that a frame be rigidly fixed to a patient's head to provide a reference point or points. Once the reference structure is attached to the patient, the image data is generated with the reference frame fixed in relation to the imaging device. That is, there is typically a mechanical coupling between the reference structure and the imaging device. After the data is collected, the patient may be removed from the scanner but the reference frame must remain attached to the patient's head. The reference frame remains attached throughout surgery so the surgeon can correlate image information about patient anatomical structures to a position within the patient's skull located with reference to the frame.

While such systems provide surgeons with a remarkable ability to locate areas of interest within a patient's brain based upon the data acquired by radiological scanners, the required reference frames are cumbersome and complicate the acquisition of radiological data. To preserve the location of the reference frame, it must remain attached to the patient's head throughout the scanning procedure and the surgical procedure. Because the reference frames may weigh several pounds and must be securely fastened to the head, they can be uncomfortable to the patient. The distances the frames extend from the patient's head also present difficulties in maneuvering the patient. Additionally, patients with larger than normal heads often cannot be fitted with stereotactic frames.

In an effort to reduce the awkwardness of the reference structure and the discomfort it causes a patient, a stereotactic system using a skull ring which may be mounted to a patient's skull was developed. The ring is a relatively small metallic circle that is attached to a patient's head using cancellous screws. Once the ring is in place, a transfer plate having two openings, one of which has a rotatable ball and socket mechanism mounted therein, is secured within the ring. The transfer plate is also provided with a radiological opaque marker which may be discerned in the radiological images generated by the scanner. The patient is then placed inside a scanner and a member extending from the ball and socket is coupled to the machine. Once the patient has been oriented within the scanner for the collection of image data, the ball and socket is locked in a fixed orientation.

Following the collection of image data, the member extending from the ring and patient which was coupled to the scanner is disconnected so the patient may be removed. The ball and socket remains locked in its orientation so the orientation of the transfer ring on the patient's skull may be later duplicated for locating a target.

After removing the transfer plate holding the ball and socket from the skull ring attached to the patient's head, the plate is attached to a member extending above a frame table to duplicate its position and orientation on the patient's head. The images generated by the scanner are viewed and the coordinate data of a selected target, such as a lesion or tumor, and the radiological marker of the transfer plate are determined. Using this coordinate data and the indicia marked on the frame table, a target marker is maneuvered on the frame table so it identifies the target position with respect to the radiological marker. A second ball and socket mechanism is placed in the second opening of the transfer plate. Thereafter, an instrument such as a biopsy probe may then be extended through the second ball and socket to the target point to define a distance and path to the target. The second ball and socket is then locked into place to preserve the orientation to the target and the distance to the target is marked on the probe.

The transfer plate bearing the second ball and socket mechanism may then be removed from the member above the frame table and reattached to the skull ring on the patient's skull with the second locked ball and socket defining a path to the selected target. Thereafter, a biopsy probe may be used to mark the patient's skull and a craniotomy performed at that point to provide an opening in the patient's skull. The biopsy probe may then be extended through the opening in the second ball and socket to the depth marked on the probe to place the biopsy probe within the lesion or tumor. In this manner, the surgeon is able to accurately place the biopsy probe without unnecessary searching to locate the tumor or lesion prior to performing the biopsy. A further description of the above technique and apparatus is given in U.S. Pat. Nos. 4,805,615 and 4,955,891 to which reference may be had.

The above-described manner for performing the biopsy facilitates the collection of image data in a number of ways.

First, the reference structure attached to the patient's skull is small in comparison to the reference frames previously used. Second, the removable plate with the ball and socket openings permit accurate location of a target area within a patient's brain prior to performing a craniotomy. Third, the removable plate with the ball and socket mechanisms ensures correct placement of the plate on the patient's skull and preserves the accuracy of the path to the target identified on the frame table. While this method greatly facilitates locating the target area within a brain, it fails to provide the surgeon with information regarding the intervening tissue area between the craniotomy opening in the skull and the target area, which lies within and possibly deeply within the brain. Furthermore, the image data generated by a scanner is not necessarily oriented transversely to the location of the opening of the ball and socket of the reference ring and thus does not provide image data at various depths between the craniotomy opening and the target area to assist the surgeon in evaluating the path to the target. Thus, while the surgeon need not search to locate the target, the surgeon does need to carefully retract the brain tissue along the path to reach the target. Otherwise, damage to any sensitive areas that may lie along the pathway is possible. The reference systems discussed above do not assist a surgeon in identifying the exact location of any such sensitive areas prior to performing the craniotomy and traversing the path to the target.

In addition to identifying the locus of the lesion or injury within the brain it is often critical to determine a suitable pathway through the brain to access that locus, in order to minimize damage to the intervening tissue. Thus, identifying the pathway to the site may be almost as critical as identifying the site itself. The above-described system has been inadequate in this respect.

In an effort to provide more automatic matching between image data and the patient as placed in surgery, systems have been developed that perform "coregistration". Coregistration is a process by which a computer matches fiducials associated with image data to fiducials associated with the patient's body. The image fiducials are typically selected by using a mouse and cursor to identify on a displayed image points that lie on a patient's skin. An articulated arm and probe are coupled to the computer to provide coordinate data for points external to the computer. Using the arm and probe, the user selects points on the patient that correspond to the selected image fiducials and the computer executes a program that matches the corresponding points. After a sufficient number of points have been selected (usually at least 8), the computer may identify the point in the displayed images that corresponds to the position of the probe proximate the patient's head. Such a system is made by Radionics of Brookline, Mass. and is identified by its product name The Operating Arm.

Such a system provides "navigational" information to a surgeon, that is, the surgeon may bring the probe to a particular location on or within a patient's head and have that location identified on the displayed image. In this way, the surgeon may view areas on the displayed image and determine their proximity to the probe location. In that manner, the surgeon may confirm the surgical approach to a target.

While these systems provide confirming navigational information they still do not project a stabilized image of the surgical path on a displayed radiological image prior to a craniotomy being performed. Such systems cannot project a stabilized path because the surgeon cannot consistently orient and stabilize the probe at exactly the same position each time the path needs to be viewed. As a consequence, such systems do not identify or persistently indicate a path to a target because the probe is operated by hand. Moreover, such systems do not ensure that the surgeon is following any path the surgeon may have selected as a result of viewing the displayed radiological images.

What is needed is a system that permits a surgeon to select, evaluate, and lock into position a path to a selected target prior to performing a craniotomy. What is needed is a system that guides a surgeon along the evaluated surgical path to a target during and after the craniotomy. What is needed is a way to select and preserve a plurality of selected paths to multiple targets after the paths have been evaluated.

SUMMARY OF THE INVENTION

These and other problems of previously known systems are overcome by a system in accordance with the principles of the present invention. This system includes an imaging display system for displaying radiological images, an image fiducial selector coupled to the imaging system for selecting fiducials on an image displayed on the display system, a target selector coupled to the imaging system for selecting a target on an image displayed on the display system, an articulated arm and probe coupled to the imaging system, which provides spatial coordinates for the probe with reference to the imaging system so thata position associated with the probe is displayed on the displayed image. A patient fiducial selector is coupled to the imaging system and to the articulated arm for selecting fiducials on a patient that correspond to the fiducials selected for the displayed image. A coregistration processor coregisters the patient fiducials to the selected image fiducials so that the coordinates provided by the articulated arm may be matched to the displayed image whereby a position of the probe may be displayed on the displayed image. A probe holder holds the probe of the articulated arm in proximity to a patient's head. the holder being selectively lockable to maintain a position proximate the patient's head. By using this system, a surgeon may evaluate the path displayed on said displayed image between said probe position and said selected target.

A system in accordance with the principles of the present invention permits a patient to be scanned without any plate or frame reference being affixed to the patient. The system coregisters image fiducials with selected anatomical features of a patient so the position of the probe may be displayed on a radiological image and a path to a selected target projected on the image. A surgeon may evaluate the path to the selected target and lock the probe position in place if the path is deemed acceptable. The surgeon may then mark the appropriate spot on the patient's head for the craniotomy. In a similar manner, the paths to other targets may be identified and marked prior to any craniotomy.

The system may further include surgical instrument collars adapted to fit within the probe holder so an instrument may be inserted through the collar in the correct orientation and position to follow the evaluated path to the selected target. Thus, the probe holder may be used to facilitate a surgeon's path selection and evaluation and then preserve that path as well as guide instruments along that path.

The system of the present invention may further include an arc carrier rod for defining a predetermined radius to a selected target. A grooved arc may be rotatably mounted to the reference rod, and the probe holder mounted in a probe adapted to slide within the grooved arc. Thus, the grooved arc may be rotated in a hemispheric fashion about the patient's head and the probe plate and holder slid along the grooved arc to define numerous entry points for evaluation by the surgeon using the radiological display system. The imaging system is further provided with a processor for interpolating data from the radiological data generated by the scanner to provide a view along the probe from any entry port selected along the hemispheric stereotactic system positioning as long as the probe reaches the holder. Utilizing this system, a surgeon may evaluate a number of entry points and select the one which presents the least risk to the patient.

Another advantage of the present system is that after a target has been selected and the biopsy or surgical procedure performed on the target, the surgeon may select a second target of interest within the patient's brain. After this selection, the probe holder may be unlocked and the probe reinserted to define a second path to the second selected target. The hemispheric stereotactic system may then be attached to provide multiple entry points to the second target for evaluation and, once a suitable path is selected, a procedure may be performed on the second target. Utilizing the system in this manner facilitates a surgery wherein radioactive seeds are implanted in various areas of a tumor with the effect that the radiation is primarily limited to the area of the tumor. This type of use also assists a surgeon in the precise placement of multiple depth electrodes in a patient's brain for monitoring.

These and other advantages of a system in accordance with the principles of the present invention may be ascertained with reference to the attached drawings and enclosed detailed description.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

The present invention may take form in various components and arrangement of components and in various steps and arrangement of steps. The drawings are only for purposes of illustrating a preferred embodiment and alternative embodiments and are not to be construed as limiting the invention.

DETAILED DESCRIPTION OF THE INVENTION

Figure 1:
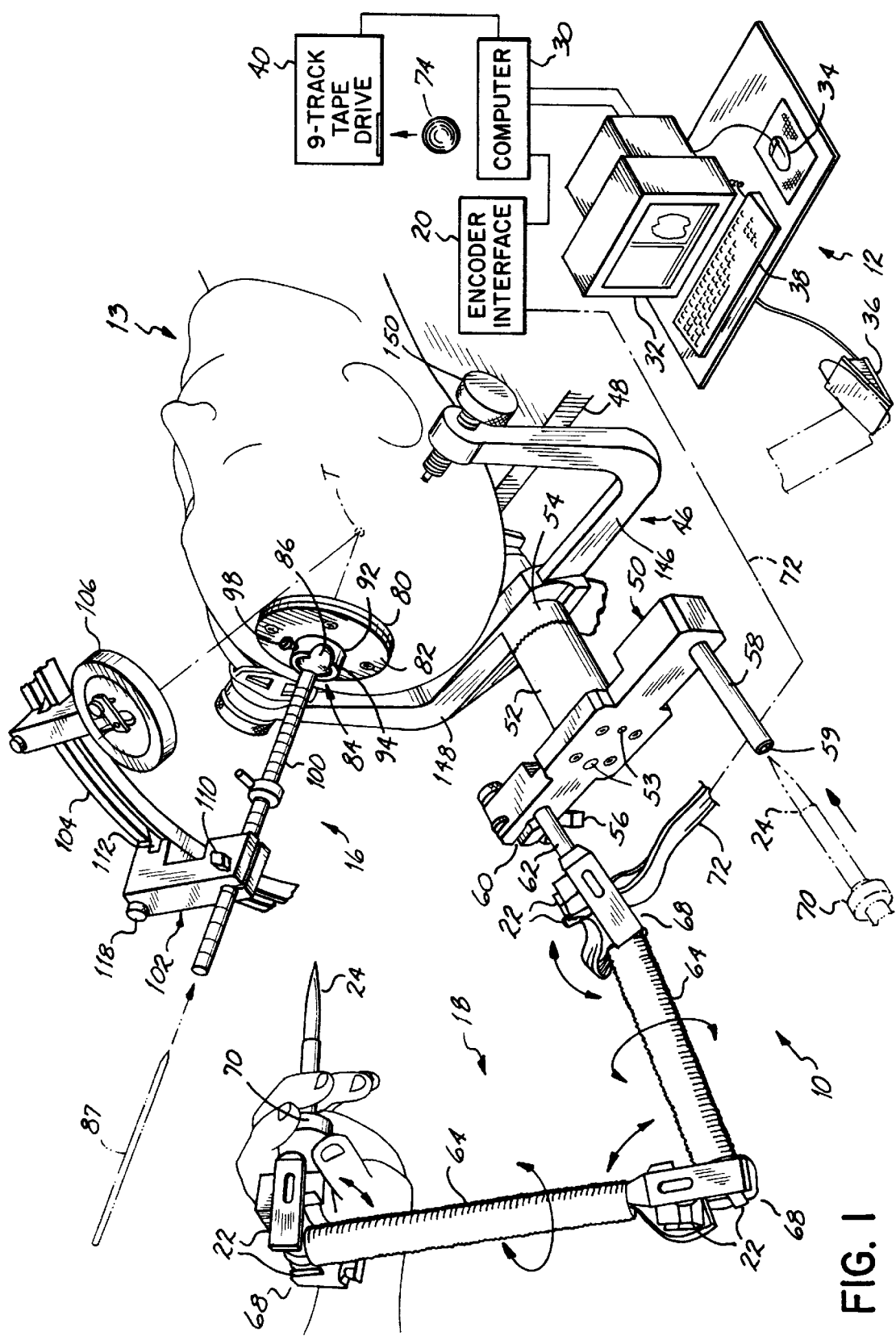
FIG. 1 is a perspective diagrammatic view of the components of one embodiment of a system in accordance with the principles of the present invention.

A neurosurgical stereotactic system 10 built in accordance with the principles of the present invention is shown in FIG. 1. The system includes an image display sub-system 12, an articulated arm and probe 18, and a stereotactic sub-system 16. The image display sub-system 12 displays images from image data generated by a scanner or from data interpolated from such data. Sub-system 12 accepts operator input for selection of fiducials, receives coordinate data from the articulated arm and probe, and coregisters selected fiducials on a patient 13 with the selected fiducials for the radiological images for the patient so that the position of the probe and a path to a selected target may be displayed. Sub-system 12 also displays an image of the articulated arm so the operation of the arm and probe may be verified.

Articulated arm and probe 18 provides spatial data to display sub-system 12 through an encoder interface 20. The spatial data is preferably generated by optical encoders 22, although other spatial coordinate data generating components may be used. Besides the data supplied by the arm and probe 18 used to locate the probe's position, probe 24 may also supply rotational data as it is rotated about its longitudinal axis to rotate the displayed image on sub-system 12, as described in more detail below.

Stereotactic sub-system 16 stabilizes the probe 24 as a surgeon guides it across a patient's head. Sub-system 16 further includes components, discussed in more detail below, that permit the probe to be locked into position, and that position utilized to guide surgical instruments to a selected target. Sub-system 16 further includes components, also discussed in more detail below, that may be used to provide multiple entry points for a surgical path to a target within the patient, all of which are centered on the selected target area. These components provide a surgeon with reasonable confidence that each probe position provided by the system is directed to the selected target.

Radiological display subsystem 12 includes a computer 30 to which a high resolution graphics monitor 32, a mouse 34, a footpedal 36, a keyboard 38 and a tape drive 40 are coupled. The computer 12 may additionally include a 3.5 inch diskette drive or the like and a digital audio tape (DAT) drive or the like. The tape drive 40 diskette drive, and DAT drive may be used to provide radiological imaging data to the computer 30. These tape drives may also be used to archive data generated by the computer 30 or to update the software which executes on the computer 30. Computer 30 may also be coupled using conventional techniques to a computer network such as an Ethernet. Such a network may be used to supply radiological image data, software, or diagnostic services.

Preferably, monitor 32 is a Multi-ScanHG Trinitron superfine pitch resolution monitor available from Sony Corporation of America. Preferably, the computer 30 is a Dell 450 DE/2 DGX manufactured by Dell Computers of Houston, Tex. The preferred tape drive 40 for reading image scan data is a 9 track tape drive manufactured by Overland Data of San Diego, Calif. The encoder interface 20 and articulated arm and probe 18 are manufactured by Immersion Human Interface Corp. of San Francisco, Calif.

Preferably, computer 30 executes the Atlas program developed by Nomos of Pittsburgh, Pa. Atlas is a computer program that displays radiological images from radiological scan data supplied by the tapes and interpolates data to provide additional views not present in the radiological scan data. The Atlas program of the preferred embodiment has been modified to accept data from the articulated arm and probe 18 through encoder interface 20. The program is loaded by using the resident operating system of computer 30 which in the preferred embodiment is the Microsoft Disk Operating System (MS-DOS). The Atlas program includes its own high level I/O routines and other computer resource functions so that the Atlas program uses the primitive level I/O operation of the resident operating system of computer 30. In the preferred embodiment, computer 30 is also provided with a telephone interface so that software and other support functions, such as diagnostics, may be provided via telephone from a remote location.

The articulated arm and probe 18 is mounted to a surgical skull clamp 46 which has been mounted to an operating table 48 (which may be of known type). Base support 50 (FIG. 1) is attached to a mounting collar 52 which is mounted to the starburst connector 54 of surgical skull clamp 46. Base support 50 is preferably mounted to collar 54 by Allen screws or the like. Preferably, the mating surfaces of collar 52 and support 50 are keyed at 53 so there is only one possible orientation of the base support 50. This feature is important in preserving reference point accuracy when the sterile base support and surgically draped arm are used as discussed in more detail below. Base support 50 also includes a lockable mounting bolt 56 at one end for the articulated arm and a hollow tubular extension 58 at its second end for holding in bore 59 the probe 24 of the articulated arm. Bolt 56 is rotatably mounted about a slot 60 cut in base support 50 for articulated arm and probe 18.

The articulated arm and probe 18 (FIG. 1) further includes a mounting stud 62, two arm members 64, and the probe 24. Joint members 68 join mounting stud 62, arm members 64, and probe 24 to form arm and probe 18. At each joint, there is rotation in two perpendicular planes to permit two degrees of freedom for each arm. The position of each arm member relative to its respective joint is preferably provided by optical encoders 22 coupled at each joint to the arm in an orthogonal relationship. Probe 24 is mounted within a collar 70 located at the outermost end of the arm so that it can rotate about its longitudinal axis. This rotational movement is used by computer 30 to rotate the radiographic images presented to the surgeon on the screen of monitor 32. Extending from one end of the articulating arm 18 is an interface cable 72 which terminates at an encoder interface 20. The encoder interface 20 converts the data from the six optical encoders 22 of the articulating arm 18 into rotated position (angular) data for the computer 30.

Tape drive 40 may be used to provide image scan data to the computer 30. Most image scanners archive image data generated from a scan by storing it on magnetic media such as a nine track tape 74. This tape may then be read by a tape drive 40 and supplied to the computer 30 which stores the data on other magnetic media such as a hard disk drive. The image data read from the tape inserted in drive 40 may be used as generated by the scanner. However, each scanner manufacturer may format the data differently. Preferably, the image data generated by the various types of scanners is converted to a standard format prior to being stored on the internal magnetic media of the computer 30. By doing so, the image display program which executes on computer 30 does not require different modules or routines for each format in order to utilize the data from various scanners.

Generally, data generated by a scanner includes image data and non-image data. Non-image data includes definition of parameters such as patient name, date, patient position, scan orientation, scan parameters, and other imaging details peculiar to each of the various scanner manufacturers. The preferred embodiment of the program executing on computer 30 extracts the basic data items common to all of the scanner manufactures and stores them with image data files in a keyword value file. The keyword value file contains a list of keywords that identify each data field and the value of that field. For example, a data field identifier for patient name is followed by the data representation of the patient's name for a series scan. These files are preferably human readable for system analysis purposes since they are not usually accessed by a user.

Image data usually includes numerical data that represents a gray scale value or some other brightness/contrast value, such as Hounsfield units, used to generate images, as is well known. These numeric values may be compressed, or expressed as integer or real number values. The preferred embodiment of the program executing on computer 30 uncompresses any compressed values and converts all of the numeric data to integer data. This data is then stored in image data files. These files are preferably written to disk in a hierarchial structure separating the patient data from one another and the image studies and series for each patient.

The footpedal 36, mouse 34, and keyboard 38 may be used by an operator to provide input to the computer 30. For example, mouse 34 may be used to manipulate a cursor on the screen of monitor 32 to select various options as discussed in more detail below. As a further example, footpedal 36 may be used by the surgeon to activate the selection of fiducials on a patient.

In the preferred embodiment, the image display program executing in computer 30 includes a graphics user interface (GUI), an input/output (I/O) library, an articulated arm interface program, and a number of application modules. The GUI interface controls the presentation of data and menus on the screen of the monitor 32. The I/O library routines perform various input and output functions such as reading image data from the tape drive 40. The articulated arm interface provides the menu and fiducial selection points displayed at the bottom of the screen on the monitor 32 of the preferred embodiment of the sub-system 12 shown in FIG. 1. Finally, the application modules execute software to perform transform operations to interpolate data for the images and to coregister the image data with the selected patient fiducials.

An alternative embodiment of stereotactic sub-system 16 that couples the articulated arm and probe 18 to the patient to permit surgical path evaluation and selection is shown in FIG. 1. That equipment includes a skull ring 80, a transfer plate 82, a swivel socket 84, and a probe alignment ball 86. This equipment is utilized by affixing the skull ring 80 to a patient's head by cancellous bone screws after the patient's scalp is shaved, prepped with betadine, and injected with xylocaine. After the skull ring is affixed, the transfer plate 82 is mounted to the skull ring by means of a post (not shown) extending from the skull ring. A swivel socket 84 is attached to the skull ring by means of Allen screws or the like. The swivel socket 84 includes a base 92 and a upwardly extending collar 94. A probe alignment ball 86 is inserted within collar 94. The probe alignment ball 86 is adapted to receive the end of probe 24. Thus, probe 24 may be inserted into the probe alignment ball 86 and the probe and ball moved together with respect to the surface of the patient's scalp.

Once a particular orientation has been selected by the surgeon based upon information provided by the radiological image displayed on monitor 32, the screws 98 extending outwardly from the collar 94 may be tightened to secure the probe alignment ball 86 in place. A surgical instrument collar of known type (not shown) may then be inserted within the probe alignment ball 86 to permit a drill or other instrument 87 (shown in phantom) to be inserted through the instrument collar to open the patient's skull. A biopsy instrument may also be inserted through the collar to the target area. Thus, use of the ring 80, transfer plate 82, socket 84, and ball 86 provide a surgeon with a stable platform for orienting probe 24 and securely locks an evaluated orientation in place to provide a guide for the surgical procedure.

The hemispheric stereotactic system used for entry site selection is also shown in FIG. 1. That equipment includes an arc carrier rod 100, a rotating support arm 102, an arc 104, and a variable collar array 106. After the probe alignment ball 86 has been oriented so probe 24 points to the target, the probe may be removed and the arc carrier rod 100 inserted into the probe alignment ball 86. The rotating support arm 102 is then mounted on the arc carrier rod 100 and secured about the rod by screw 110. A grooved tongue or key 112 is mounted in lockable relationship on the rotating support arm 102 and is adapted to fit within a track cut within arc 104. By tightening screw 118 of the rotating supporting arm 102, the arc 104 may be secured to arm 102 anywhere along the length of arc 104. Variable collar array 106 is likewise adapted to have a bit that is slidably received in arc 104 and may be locked into place anywhere along the length of arc 104. Collar 106 also has a receptacle that receives the probe 24 so a surgeon may evaluate a path to the selected target by viewing the path displayed on the monitor 32 of sub-system 12. Because carrier rod 100 points to the target, the support arm 102 and arc 104 may be rotated about the patient's head in a hemispheric fashion that is centered about the target. Preferably, support arm 102 is locked into position about the arc carrier rod 100 so that a central opening in the variable collar array 106 is located approximately 19 centimeters from the target about which the arc 106 is centered.

The components of the hemispheric stereotactic system permit a surgeon to maneuver the probe 24 about a patient's head with a reasonable degree of confidence that the receptacle is directed to the previously selected target. By simply swinging the arc 104 around rod 100 and sliding the collar 106 within arc 104, the surgeon is provided with numerous sites for evaluation which may be locked in place as a surgical guide.

Figure 3:
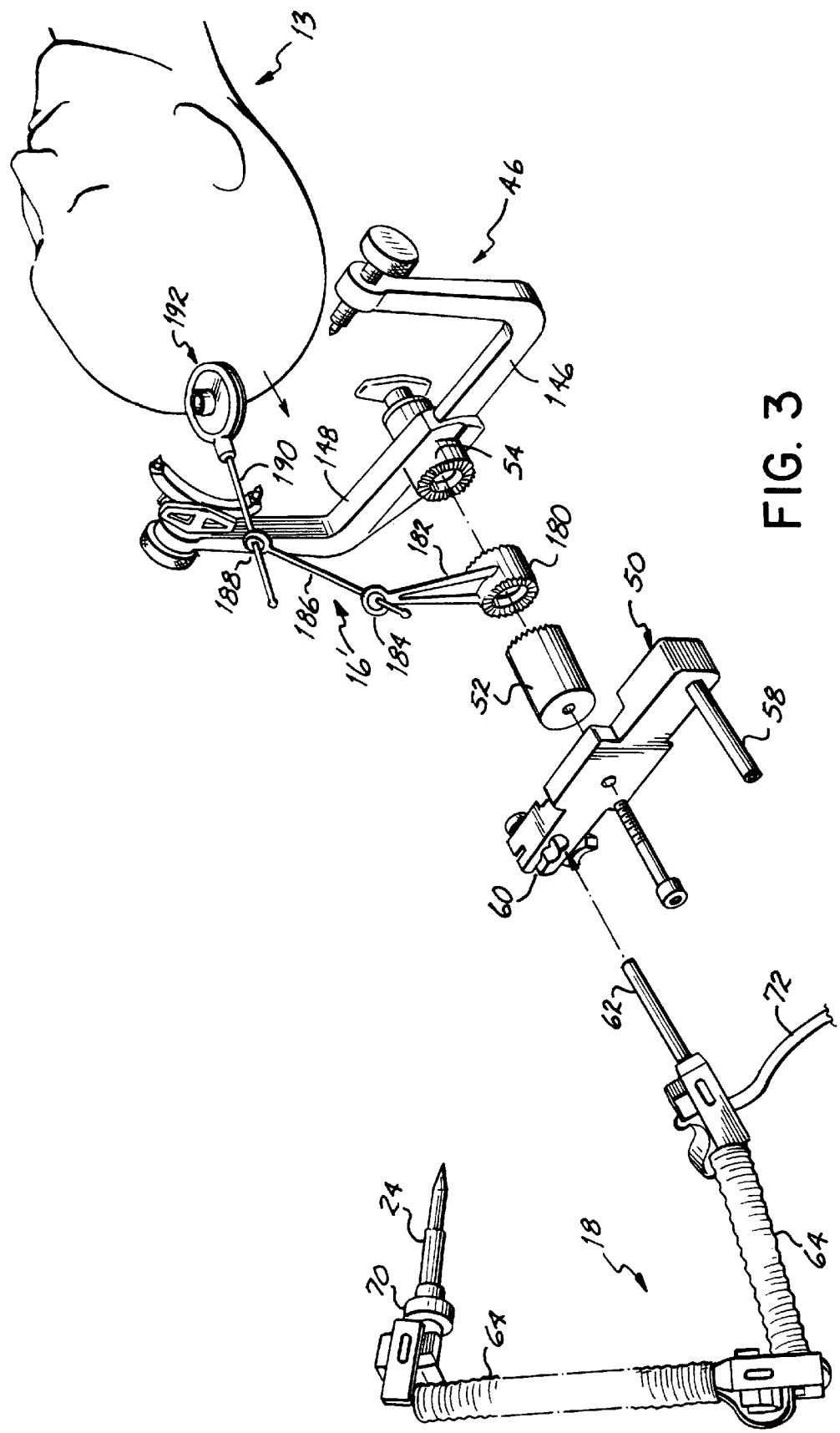
FIG. 3 is a view of the preferred embodiment of a stereotactic sub-system for use in the system of FIG. 1.

The preferred embodiment of stereotactic system 16 is shown in FIG. 3. That system includes a probe holder collar 180 and a rigid offset arm 182 which is interposed between sunburst connector 54 and collar 52. Offset arm 182 terminates in a pivot joint 184 from which an adjustable arm 186 extends. Another adjustable arm 190 extends from a pivot joint 190 at the end of arm 186. Arm 188 terminates in to a probe holder 192 which is provided with a transfer plate 82 ball and socket mechanism 84 and adjustment ball 86, as already described in connection with FIG. 1. Thus, subsystem 16 provides a rigid, adjustable arm by which the probe holder 192 and attendant components may be maneuvered about a patient's head and then selectively locked into position for path evaluation, surgical instrument guidance, or attachment of the hemispheric system.

To use the system 10 for a neurosurgery, a patient 13 is scanned in an image scanner to create a series of images. A "series" may be a group of parallel, equally spaced images, sometimes called "slices", of a volumetric portion of a patient's body. Preferably, the images comprising the series are contiguous. A group of more than one series of images is commonly referred to as a "study" or "suite" and may also be utilized by the system. Examples of series are axial, coronal, rotating, and sagittal. An axial series is from the top of the patient's head to the base of the skull, a coronal series is from the face to the back of the patient's head, rotating series is around a patient's head, and a sagittal series are sideviews of the patient's head to the other side. Preferably, the series is generated with a gantry angle of 0°, otherwise the data interpolation performed by the preferred embodiment of the Atlas program may be distorted.

After the series is generated by the scanner, it may be written to magnetic media for transportation to system 10. Typically, the image data is written to a nine track tape 74 which may be read by the nine track magnetic tape reader 40. The user may activate computer 30 and activate the nine track tape interface program in the I/O library. By using this program, a user may read the image data from the nine track tape 74 into the computer 40 which then stores the data in an appropriate format to a hard drive or the like. Computer 30 may also receive data from an image scanner by means of the DAT reader, diskette drive, a computer network, or the like.

Figure 2:
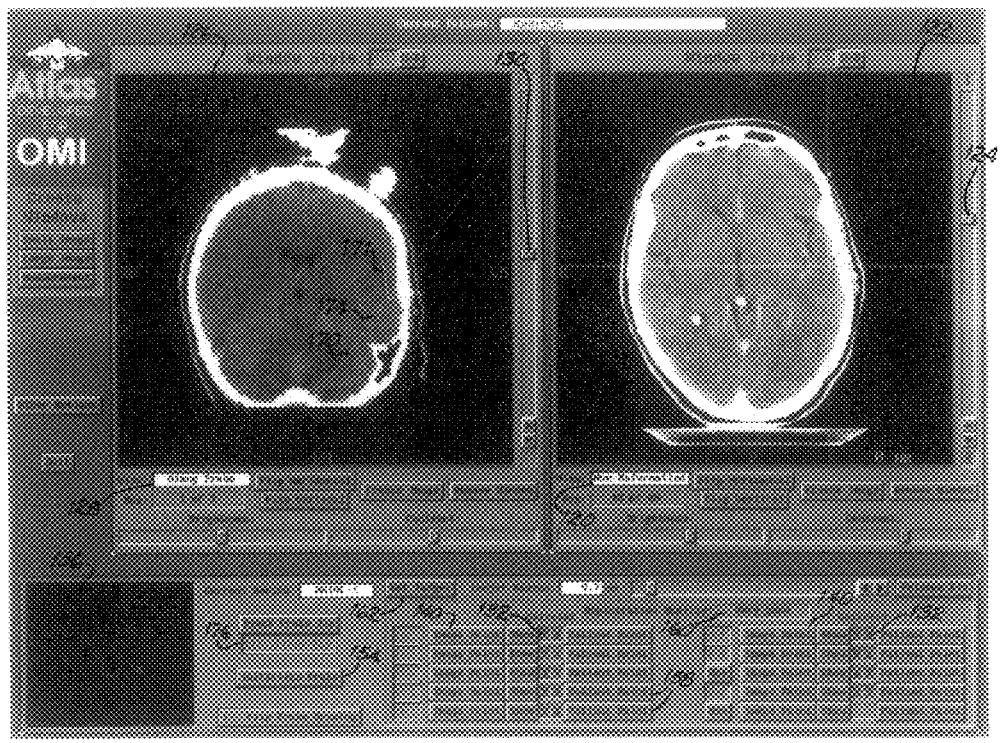
FIG. 2 shows a representative screen displaying image information generated by the system of FIG. 1.

After the image data is read into the computer's memory, the user may execute the program which displays the image radiological data in a display window on the monitor 32. The user may select a particular view by clicking on the view icon 120 of the screen shown in FIG. 2. That action causes a menu to be displayed for various series or views from which the user may select. After a series has been selected, the first image or slice of the series is presented in the display window 122 as shown in FIG. 2. The user may view each of the images in the series by manipulating the slider 124 button on the screen with the mouse 34.

The user may select a second series to be displayed in a second display window 126. After creating the second display window by clicking on the view icon 128 for the second window, the user may select the particular series to be displayed in that window and likewise view the various slices by manipulating the slider button 130 with the mouse 34.

Computer 30 also may generate a second series that was not generated by the scanner. The computer 30 does this by interpolating data from one of the series generated by the scanner to generate the second series. For example, a coronal series may be generated by the scanner and displayed in the first display window of the system. If the user selected a sagittal series, which was not generated by the scanner, for display in the second window, the system interpolates the data at the righthand edge at each of the coronal images and generates a sagittal view from that data. This process is repeated for equally spaced, parallel images from the sagittal coronal perspective to create the second sagittal series.

In the preferred embodiment, the Atlas program reformats the image data to generate data that represents a volumetric representation of the scanned area. This is done by interpolating the image data for the individual slices to generate additional "slices" not acquired by the scanner. Preferably, this is done by generating so-called "voxel" values that represent an image value that is cubic in dimension, although other volumetric shapes may be used. For example, if the series is made of images that represent 3 mm slices and each pixel value represents a 0.5 mm×0.5 mm, the interpolated voxels preferably represent a cube which is 1 mm×1 mm×1 mm. To interpolate the voxel values for the voxels in the plane of the image, each group of four adjacent pixels forming a square are averaged and the resulting averages comprise the data to form the in plane image of 1 mm×1 mm×1 mm voxels. For the voxels that represent the planes at the 2 mm and 3 mm depths, the inplane voxel image is preferably combined with the underlying image plane (reference plane) at the next lower 4 mm plane using a linear weighing proportional to the distance from the selected plane to the reference plane. Of course, other interpolation schemes may be used as are well known in the art. After the interpolated data is generated, Atlas uses the data to generate any series requested by a user.

Once the display window or windows are created and an appropriate image series displayed within those windows, the user may select image fiducial points. This is done by clicking the mouse on the appropriate areas within the image fiducial point identifier menu as shown in FIG. 2. After activating one of the image point icons 140, the user may use the mouse 34 to manipulate a cross-hair cursor across the image and after centering it on a particular feature, clicking on the mouse button to cause the program executing in computer 30 to match the point on the image with the selected image point icon 132. The user may do this for, say, eight points, although fewer or more points may be implemented in a system in accordance with the principles of the present invention. At least three points are needed before coregistration may occur and, most preferably, coregistration is best achieved with approximately eight to ten points.

The mounting collar 52, base support 50, and articulated arm and probe 18 are mounted to the skull clamp 46 holding the patient's head. Preferably, the skull clamp 46 is one manufactured by Ohio Medical Instrument Co., Inc. of Cincinnati, Ohio and designated as a modified MAY-FIELD® clamp. The clamp includes a ratchet arm 146 mounted within a sleeve arm 148 and further includes a two pin bracket (not shown) mounted to the sleeve arm and a torque screw and pin 150 mounted to the ratchet arm 146. This clamp is adjusted to fit the patient's head by well known procedures.

Located on the sleeve arm is a starburst connector 54 to which the mounting collar 52 is mounted. Base support 50 for the articulated arm and probe 18 is attached to the mounting collar 52 by means of Allen screws or the like. The articulated arm and probe 18 are attached to the base support 50 as discussed above and the probe 24 is placed in the tubular extension 58 of the base support in preparation for probe initialization (shown in phantom in FIG. 1).

In the preferred embodiment, the user must place the articulated arm so that all the side mounted optical encoders are on the same side of each arm segment. If the arm is placed in an incorrect position, the computer 30 and encoder interface 20 interpret the angular data from the articulated arm as being in a direction opposite that of its actual movement and improperly display the probe's position. Once the arm is the appropriate location, the probe may then be initialized.

By clicking on the probe initialization icon 154 (FIG. 2), the user permits the computer 30 to begin accepting angular data input from the articulated arm and probe 18 and to initialize the probe's position within extension 58 as a reference point. A display area 156 is shown on the lower left portion of the screen on the monitor 32 which demonstrates the position of each arm segment and the tip of the probe 24. By retracting the probe 24 from the tubular extension 58, the user may manipulate the articulated arm and probe tip in space and observe its movement on the screen. In this way, the user can verify that the optical encoders 22 were in the correct position for initialization by noting the upward movement of the probe on the screen when the probe is moved in an upwardly vertical position, for example. If the displayed probe moves in a direction opposite that in which the probe tip is actually moved, then the user knows that the arm was initialized incorrectly and should repeat initialization with the articulated arm in the proper position.

After confirming that the probe was properly initialized, the user may then place the probe tip on the external points of the patient's skull that correspond to the image fiducials previously selected. Typically, these points include the bridge of the nose aligned with the center of the eye sockets or the like. This is done by having the user first click on the select button adjacent a patient point icon 158 and then placing the probe 24 at a point on the patient's skull that corresponds to the image fiducial associated with the activated patient point. By depressing the footpedal 36, the coordinates of the patient fiducial identified by the probe's position are associated with the activated patient point. The reader should note that the selection of the patient fiducials may precede the selection of the image fiducials.

After the user has selected at least three patient and image fiducial points, computer 30 begins to execute a program to coregister the radiological display data with the selected patient fiducials. Preferably, the program implements an iterative algorithm for performing the coregistration. An indicator window 160 is provided on the screen of monitor 32 (FIG. 2) to provide the user with information regarding the quality of the coregistration between the radiological data and the selected patient fiducial points. Typically, the coregistration improves with the number of selected points and the number of approximately eight to ten points normally provides excellent registration between the patient and the image data.

Preferably, coregistration is preformed by an iterative algorithm implemented in one of the program modules executing on computer 30. The preferred algorithm selects a set of image fiducial points and the corresponding patient fiducial points. The centroids of the geometric figures defined by each selected set are computed. The coordinates of one of the centroids are then translated to the coordinates of the second centroid and the points associated with the first centroid are likewise translated. The differences in coordinates of the translated and untranslated points for the first set are squared to determine an overall error value or merit figure. The translated points are then changed an incremental amount in one direction only and the difference between the points in the first set and their corresponding points in the second set are calculated and squared. If the error result is less than the merit figure then the incremented value becomes the point values for the first set and the error result becomes the new merit figure.

The incremental change is again performed in the same direction and a new error result calculated. When the error result is greater than the current merit figure, the translated points are deemed the best fit.

The incremental change now is computed and evaluated for another direction. Incremental changes in the second direction continue until the error result is greater than the merit figure and the previously translated point deemed the best fit. The incremental changes then continue in the previous direction until the error result is greater than the current merit figure. The incremental changes again are tested for the second direction. This process continues until no translation in either direction generates an error result less than the current merit figure. When this occurs, the third direction is incrementally changed and tested using the error result and merit figure computed as described above When no incremental change in any direction produces an error result greater than the current merit figure, the coregistration is complete and translation of all points in one set to corresponding coordinates in the second set may be performed.

Sometimes a patient fiducial does not correspond accurately with the point selected in the image data and may degrade the rating of the coregistration. The deactivation of such a point, by resetting the corresponding "use" icon, may improve the coregistration rating. Computer 30 permits a user to selectively activate and deactivate points to determine which points provide the best registration between the patient and the image data. The reader should note that coregistration improves with the number of fiducial points, however, so the better action is to reselect one of the image or patient fiducials so it better corresponds to its mate.

Either prior to the coregistration or following it, the user may select a target. This is done by activating the set target icon 162 on the screen of monitor 32 with the mouse 34 and moving cursor cross-hairs with the mouse to an area within the interior of the patient's head displayed within the image.

Typically, the area of interest may be a tumor, a lesion, a suspected point of activity for which a surgeon wishes to place a depth electrode, or an area for the implantation of a radioactive "seed" for radiosurgery. The target coordinates are established by clicking on the set target icon 162.

After coregistration and target selection have been performed, the user may the place the probe 24 anywhere on the patient's skull (so long as that area was part of the area scanned in the scanner), and a path 170 is displayed from that point (marked by the arrowhead 172) to the target (marked by the cross-hairs 174). The path to the target is preferably displayed to indicate whether the path is actually present on the image slice being displayed at that time. For each position, the distance between the probe position and the selected target along the displayed path is shown in the lower right corner of the display window (FIG. 2). For example, a surgeon may place the probe at a point which is shown on an image slice presently being displayed. However, the surgeon may be holding the probe at an orientation such that the path from the probe 24 to the target would traverse one or more slices prior to arriving at the target. In that case, the area actually present on the slice being displayed is preferably shown in yellow and the remainder of the path to the target is preferably shown in red (FIG. 2). By manipulating the slider button 130 with the mouse 34, the surgeon may view each portion of the target path in the appropriate image slice until the target is reached to evaluate the tissue that the selected path traverses. If the surgeon decides that the path presents risks that are unacceptable, the surgeon may select a different orientation or different point on the patient's skull and re-examine the path.

By selecting the view "across the probe", a series is shown in the second display window which may be manipulated by using the mouse 34 to move the slider button 130 for that display window. In this manner, the images of the planes transverse to the probe 24 are shown from the probe 24 to the target area. In this way, the surgeon may evaluate the path through the patient's brain tissue to get to the target.

Once the surgeon has selected a particular path to the selected target, a skull ring 80 may be attached to the patient's head and a transfer plate 82 installed on the skull ring 80. The transfer plate 82 includes a probe alignment ball 86 in which the probe 24 may be located. After the probe 24 is placed within the ball 86, it may be moved to again select the path to the target area which is optimal in the surgeon's opinion. While holding the probe 24 at that location, the ball 86 may be locked into position to define a path to target and the probe removed. Preferably, the apparatus shown in FIG. 3 is used to avoid attaching skull ring 80 to the patient's head.

Preferably, a second support base 50 and probe 24 that may be sterilized replace the support base and probe used for fiducial identification and coregistration. The support base and probe that may be sterilized is preferably made from gray anodized aluminum and the non-sterilized base and probe are made from black anodized aluminum. Preferably, the sterilizable version of the tubular extension 58 and probe 24 are shorter than the non-sterilizable counter-parts to facilitate sterilization. However, the mounting collar 70 of probe 24 attaches to the probe mounting stud extending from the outermost joint of the articulated arm at a second location to ensure the reference point used for coregistration is not disturbed.

The sterilizable base support is mounted to collar 52 after a sterilized surgical drape with an opening cut therein is placed over the collar 52. Prior to mounting articulated arm and probe 18 to the base support 50, a sterilized tubular drape is placed over the arm and mounting stud 62. Probe mounting collar 70 is then placed over the tubular drape to affix the sterilizable probe 24 in place. The probe is then returned to the extension 58 and the user clicks on the gray probe icon 176 (FIG. 2) so the Atlas program may adjust for the length of the probe 24. The thickness of the surgical drapes are compensated in the machinery of the sterilization parts. That is, the opening in the mounting collar is enlarged an appropriate amount to compensate for the surgical drape between the mounting post and collar. This compensation is required to ensure that the screws used to lock the probe to the post do not pull the probe tip off of the center line of the post. The user then clicks on the initialization probe icon 154 to verify arm placement. Coregistration is automatic using the previously selected fiducials.

At this point, the surgeon may use an appropriate drill to open the patient's skull and insert an instrument collar into the transfer plate 82. The surgeon could then insert, for example, a biopsy needle directly to the target at the indicated depth and be reasonably confident that the biopsy needle is at the target area having passed through only the tissue viewed in the images displayed in the display window. Following the procedure, the surgeon may close the opening or further treat the target area. Likewise, the surgeon may select other targets and treat them as the first one was.

After mounting the skull plate 80 and locking the ball 86 of plate 82 into position, the surgeon may decide to mount an arc rod to provide a hemispheric instrument positioning system that is centered about the target area. This is done by attaching the arc rod 100 to the ball 86, mounting the rotating support arm 102 to the rod 100 and attaching the arc 104 to the support arm 102. The variable array 106 is then mounted to the arc 104 and a position may be selected anywhere about the hemisphere by rotating the support arm 102 about the rod 100, sliding the arc 104 with respect to the support arm 102, or by moving the variable array 106 along the arc 104. At any of these points, the surgeon may be reasonably confident that he has located a point that is centered about the target area.

While the present invention has been illustrated by the description of an alternative embodiment, and while the embodiments have been described in considerable detail, it is not the intention of the applicant to restrict or in anyway limit the scope of the appended claims to such detail. Additional advantages and modifications will readily appear to those skilled in the art. For example, both MRI and CT images may be loaded into computer 30 and coregistration between them may be achieved prior to coregistration with the patient. This provides the surgeon with the organ details from the NMR scan and the coordinate accuracy of the CT scan. The invention in its broadest aspects is therefore not limited to the specific details, representative image system and illustrative examples shown and described. Accordingly, departures may be made from such details without departing from the spirit or scope of applicant's general inventive concept.

What is claimed is:

1. A tooling support for use during a stereotactic procedure performed on a patient supported by a patient support comprising:

a support apparatus adapted to connect to the patient support; and a tool holder mounted to the support apparatus and movable to selected positions proximate the patient, the tool holder comprising an alignment element rotatably mounted on the tool holder and adapted to receive a tool, the alignment element being selectively rotatable to change an orientation of the alignment element without changing its position with respect to the patient, thereby defining a path between the tool and a target point within the patient, and a clamp operably mounted with respect to the alignment element for selectively locking the alignment element in the tool holder at an orientation directing the tool along the path.

2. The tooling support of claim 1 wherein the support apparatus comprises one end adapted to be connected to the patient support and an opposite end connected to the tool holder.

3. The tooling support of claim 2 wherein the patient support includes a skull clamp and the one end of the support apparatus is mounted to the skull clamp.

4. The tooling support of claim 2 wherein the patient support includes a table and the one end of the support apparatus is mounted to the table.

5. The tooling support of claim 1 wherein the tool that the alignment element is adapted to receive is a probe coupled to a spatial coordinate generator.

6. The tooling support of claim 1 wherein the support apparatus comprises an adjustable arm assembly.

7. The tooling support of claim 6 wherein the adjustable arm assembly comprises at least two arms.

8. The tooling support of claim 6 wherein the support apparatus further comprises:

a first shaft having one end adjustably coupled to the patient support; and a second shaft having one end rotatably connected to an opposite end of the first shaft to permit the second shaft to be oriented at an angle with respect to the first shaft, whereby the tool holder is selectively moved to a desired position by adjusting the positions of the first and second shafts.

9. The tooling support of claim 8 further comprising a block adapted to be mounted to the patient support and coupled to the one end of the first shaft.

10. The tooling support of claim 9 wherein the block is rotatably coupled to the one end of the first shaft.

11. A tooling support for use during a stereotactic procedure performed on a patient supported by a patient support comprising:

an adjustable arm assembly having one end adapted to connect to the patient support; and a tool holder mounted on an opposite end of the adjustable arm assembly and movable to selected positions proximate the patient, the tool holder comprising a generally spherical alignment element rotatably mounted on the tool holder and adapted to receive a tool, the alignment element being pivotable with respect to the tool holder to define a path between the tool and a target point within the patient, and a clamp operably mounted with respect to the alignment element for selectively locking the alignment element in the tool holder at an orientation directing the tool along the path.

12. A tooling support for use during a stereotactic procedure performed on a patient supported by a patient support comprising:

a mount adapted to connect to the patient support;

a first shaft having one end adjustably coupled to the mount;

a second shaft having one end adjustably coupled to an opposite end of the first shaft to permit the second shaft to be oriented at different angles with respect to the first shaft; and a tool holder mounted at an opposite end of the second shaft and adapted to receive a tool, the tool holder including an alignment element rotatably mounted in the tool holder and adapted to receive a tool at a desired position with respect to the patient, the alignment element being selectively adjustable to move the tool to an orientation directing the tool along a path between a target point within the patient; and a clamp operably connected to the alignment element for selectively locking the alignment element with respect to the tool holder at the orientation directing the tool along the path.

13. An apparatus for use during a stereotactic procedure comprising:

a skull clamp for holding a patient's head in a desired position;

an arm having a first end connected to the skull clamp; and a probe holder mounted on the arm and adapted to hold a probe, the arm being movable to locate the probe holder in proximity to a patient at a desired position, the probe holder being pivotable at the desired position with respect to the patient to allow a surgeon to evaluate and establish a desired path between the desired position and a target located in the head of the patient, the probe holder being lockable to fix the probe holder supporting the probe at a desired orientation directing the probe along the desired path.

14. The apparatus of claim 13 wherein the probe holder comprises a ball and socket mechanism, the ball being lockable within the socket.

15. The apparatus of claim 13 wherein the arm further comprises at least two adjustable arms adjustably supporting the probe holder with respect to the skull clamp.

16. The apparatus of claim 13 wherein the probe holder is also adapted to receive an instrument in a manner so as to align the instrument with the target along the desired path.

17. A stereotactic guide device for use with a neurosurgical headclamp comprising an arm having a proximal end and a distal end, an attachment device carried by the proximal end for securing the arm to the headclamp in a spacial position close to a patient's head, a chuck device secured to the distal end of the arm, the chuck including an external body and a ball freely rotatable about its center in the external body, the ball capable of axially guiding an elongated surgical instrument therethrough, and a locking device to releasably lock the ball in a selected orientation relative to the external body.

18. An apparatus for use during a stereotactic surgical procedure, the apparatus comprising:

a probe holder having a swivel socket,
an alignment ball moveably inserted into the swivel socket, the alignment ball having a bore adapted to receive a surgical tool, and
a screw extending through the swivel socket for locking the alignment ball within the swivel socket; and an arm assembly having a first end adapted to mount the apparatus to a skull clamp fixed to the head of a patient,
a second end terminating into the probe holder, and
adjustable arms and joints for adjusting the probe holder at a desired position with respect to the head of the patient.

19. The apparatus of claim 18 wherein the arm assembly comprises a sunburst connector connectable to the skull clamp.

20. The apparatus of 19 wherein the adjustable arms comprise a rigid offset arm having one end extending from the starburst connector.

21. The apparatus of claim 20 wherein an opposite end of the rigid offset arm is rotatable connected to another adjustable arm.

22. The apparatus of claim 18 wherein the adjustable arms comprise
- a first adjustable arm extending from a joint connected to the skull clamp; and
- a second adjustable arm extending from a joint on the first adjustable arm.

23. The apparatus of one of the claims 22 wherein the second adjustable arm terminates in the probe holder.

24. A tooling support for use during with an imaging system during a stereotactic procedure being performed on a patient comprising:
- a tool holder locatable at a desired position with respect to the patient, the tool holder comprising
  - an alignment element rotatably mounted on the tool holder and being selectively rotatable to change an orientation of the alignment element without changing its position with respect to the patient, and
  - a clamp operably mounted with respect to the alignment element for selectively locking the alignment element,
  - the alignment element adapted to support a probe and being pivotable at its position with respect to the patient to allow a surgeon to evaluate and establish a desired path as displayed on the imaging system between the probe and a selected target point, the alignment element being lockable with the clamp to fix the alignment element supporting the probe at a desired orientation directing the probe along the desired path, and thereafter, upon removing the probe, the alignment element adapted to receive an instrument, and the alignment element providing independent of the imaging system, support and guidance for the instrument so that the instrument follows the desired path.

25. The tooling support of claim 24 wherein the tool holder is attached to the patient.

26. The tooling support of claim 24 wherein the tool holder is attached to a patient support.

27. The tooling support of claim 26 wherein the tool holder is mounted to a patient support.

28. A tooling support for use with an imaging system during a stereotactic procedure performed on a patient comprising a tool holder adapted to be mounted at a desired position on a patient, the tool holder comprising a lockable, rotatable alignment element adapted to support a probe connected to the imaging system and being pivotable at the desired position with respect to the patient to allow a surgeon to evaluate and establish a desired path as displayed on the imaging system between the probe and a selected target point, the tool holder being lockable to fix the tool holder supporting the probe at a desired orientation directing the probe along the desired path, and thereafter, upon removing the probe, the tool holder adapted to receive an instrument, and the tool holder providing independent of the imaging system, support and guidance for the instrument so that the instrument follows the desired path.

29. A tooling support for use with an imaging system during a stereotactic procedure performed on a patient comprising a tool holder adapted to be mounted at a desired position with respect to a patient, the tool holder comprising a lockable, rotatable alignment element adapted to support a probe connected to the imaging system and being pivotable at the desired position with respect to the patient to allow a surgeon to evaluate and establish a desired path as displayed on the imaging system between the probe and a selected target point, the tool holder being lockable to fix the tool holder supporting the probe at a desired orientation directing the probe along the desired path, and thereafter, upon removing the probe, the tool holder adapted to receive an instrument, the tool holder providing independent of the imaging system, support and guidance for the instrument so that the instrument follows the desired path.

30. A method for using a tool holder and an imaging system for evaluating and securing a surgical path to a target point within a patient comprising:
- releasably securing a tool holder with respect to a patient;
- supporting a probe in the holder;
- displaying a path on the imaging system extending from the probe;
- rotating an alignment element on the tool holder to a desired orientation causing the path being displayed on the imaging system to extend from the probe to the target point;
- releasably locking the alignment element at the desired orientation; and
- removing the probe and inserting an instrument, the tool holder providing independent of the imaging system, support and guidance for the instrument so that the instrument follows the desired path.

31. The method of claim 30 further comprising releasably securing the tool holder to the patient.

32. The method of claim 30 further comprising releasably securing the tool holder to a patient support.

* * * * *

UNITED STATES PATENT AND TRADEMARK OFFICE
CERTIFICATE OF CORRECTION

PATENT NO. : 6,261,300 B1
DATED : July 17, 2001
INVENTOR(S) : James L. Day

It is certified that error appears in the above-identified patent and that said Letters Patent is hereby corrected as shown below:

Title page,
Inventors, please correctly identify the sole inventor to read
-- [75] Inventor: James L. Day, Cincinnati, OH (US) --.

Column 1,
Line 2, "filed on Dec. 6, 1997 U.S. Pat. No." should read -- filed on Dec. 6, 1997, now U.S. Pat. No. --.

Column 4,
Line 26, "so thata position" should read -- so that a position --.
Line 36, "to a patient's head. the" should read -- to a patient's head, the --.

Column 6,
Line 25, "the tape drive 40 diskette" should read -- the tape drive 40, diskette --.

Column 7,
Line 52, "of the scanner manufactures" should read -- of the scanner manufacturers --.

Column 9,
Line 26, "system 16 " should read -- system 16' --.
Lines 33-34, "transfer plate 82 ball" should read -- transfer plate 82, ball --.
Line 36, "system 16 " should read -- system 16' --.

Column 11,
Line 31, "Once the arm is the appropriate" should read -- Once the arm is in the appropriate --.

Column 12,
Line 12, "coregistration is preformed" should read -- coregistration is performed --.
Line 45, "as described above When" should read -- as described above. When --.

Column 13,
Line 7, "the user may the place" should read -- the user may then place --.

UNITED STATES PATENT AND TRADEMARK OFFICE
CERTIFICATE OF CORRECTION

PATENT NO. : 6,261,300 B1
DATED : July 17, 2001
INVENTOR(S) : James L. Day

It is certified that error appears in the above-identified patent and that said Letters Patent is hereby corrected as shown below:

Column 17,
Line 4, "The apparatus of 19" should read -- The apparatus of claim 19 --.
Line 8, "is rotatable connected" should read -- is rotatably connected --.
Line 18, "A tooling support for use during with" should read -- A tooling support for use with --.

Signed and Sealed this

Seventh Day of May, 2002

*Attest:*

JAMES E. ROGAN
*Director of the United States Patent and Trademark Office*

*Attesting Officer*